US006270779B1

(12) United States Patent
Fitzhugh et al.

(10) Patent No.: US 6,270,779 B1
(45) Date of Patent: Aug. 7, 2001

(54) NITRIC OXIDE-RELEASING METALLIC MEDICAL DEVICES

(75) Inventors: Anthony L. Fitzhugh, Frederick, MD (US); Peiwen Cheng, Santa Rosa, CA (US); Joseph Saavedra, Thurmont, MD (US); Robert Cafferata, Belmont, MA (US); Marc Hendriks, Brunssum (NL); Larry K. Keefer, Bethesda, MD (US); Eugene Tedeschi, Santa Rosa, CA (US); Michel L. P. M. Verhoeven, Maastricht (NL)

(73) Assignee: United States of America, Washington, DC (US)

( * ) Notice: Subject to any disclaimer, the term of this patent is extended or adjusted under 35 U.S.C. 154(b) by 0 days.

(21) Appl. No.: 09/567,579

(22) Filed: May 10, 2000

(51) Int. Cl.[7] ............................ A61K 9/00; A61K 33/00; A61K 31/74; A61F 13/00; A61F 2/00

(52) U.S. Cl. ........................ 424/400; 424/718; 424/422; 424/423; 424/78.27

(58) Field of Search ................................ 424/400, 78.27, 424/718, 422, 423; 600/36; 524/429; 385/12; 422/44; 514/772.4

(56) References Cited

U.S. PATENT DOCUMENTS

| 4,954,526 | 9/1990 | Keefer . |
| 5,039,705 | 8/1991 | Keefer et al. . |
| 5,155,137 | 10/1992 | Keefer et al. . |
| 5,212,204 | 5/1993 | Keefer et al. . |
| 5,229,172 | 7/1993 | Cahalan et al. . |
| 5,250,550 | 10/1993 | Keefer et al. . |
| 5,268,465 | 12/1993 | Bredt et al. . |
| 5,366,997 | 11/1994 | Keefer et al. . |
| 5,380,758 | 1/1995 | Stamler et al. . |
| 5,405,919 | 4/1995 | Keefer et al. . |
| 5,428,070 | 6/1995 | Cooke et al. . |
| 5,468,630 | 11/1995 | Billiar et al. . |
| 5,482,925 | 1/1996 | Hutsell . |
| 5,519,020 | 5/1996 | Smith et al. . |
| 5,525,357 | 6/1996 | Keefer et al. . |
| 5,574,068 | 11/1996 | Stamler et al. . |
| 5,583,101 | 12/1996 | Stamler et al. . |
| 5,632,981 | 5/1997 | Saavedra et al. . |
| 5,650,447 | 7/1997 | Keefer et al. . |
| 5,658,565 | 8/1997 | Billar et al. . |
| 5,676,963 | 10/1997 | Keefer et al. . |
| 5,683,668 | 11/1997 | Hrabie et al. . |
| 5,691,423 | 11/1997 | Smith et al. . |
| 5,700,830 | 12/1997 | Korthuis et al. . |
| 5,714,511 | 2/1998 | Saavedra et al. . |
| 5,718,892 | 2/1998 | Keefer et al. . |
| 5,721,365 | 2/1998 | Keefer et al. . |
| 5,770,645 | 6/1998 | Stamler et al. . |
| 5,789,447 | 8/1998 | Wink, Jr. et al. . |
| 5,814,656 | 9/1998 | Saavedra et al. . |
| 5,814,667 | 9/1998 | Mitchell et al. . |
| 5,837,736 | 11/1998 | Mitchell et al. . |
| 5,840,759 | 11/1998 | Mitchell et al. . |
| 5,877,216 | 3/1999 | Place et al. . |
| 5,891,459 | 4/1999 | Cooke et al. . |
| 5,910,316 | 6/1999 | Keefer et al. . |
| 5,945,452 | 8/1999 | Cooke et al. . |
| 5,958,427 | 9/1999 | Salzman et al. . |
| 5,962,520 | 10/1999 | Smith et al. . |
| 5,994,444 | 11/1999 | Trescony et al. . |
| 6,024,918 | 2/2000 | Hendriks et al. . |
| 6,171,232 | * 1/2001 | Papandreou et al. .................. 600/36 |

FOREIGN PATENT DOCUMENTS

WO 00/02501  1/2000 (WO) .

OTHER PUBLICATIONS

Keefer, et al; "NONOates" (1–Substituted Diazen–1–ium–1, 2–diolates) as Nitric Oxide Donors: Convenient Nitric Oxide Dosage Forms. Methods in Enzymology, vol. 268: 281–293.

Saavedra, et al.; "Conversion of Polysaccharide to Nitric Oxide–Releasing Form Dual–Mechanism Anticoagulant Activity of Diaseniumdiolated Heparin." Bioorganic & Medicinal Chemistry Letters 10 (2000) 1–3.

Hrabie, et al; "New Nitric Oxide–Releasing Zwitterions Derived from Polyamines." J. Org. Chem. 1993, 58, 1472–1476.

Chandy et al; "Use of Plasma Glow for Surface–Engineering Biomolecules to Enhance Bloodcompatibility of Dacron and PTFE Vascular Prosthesis." Biomaterials 21: 669–712.

Drago, Russell S.; "Free Radicals in Inorganic Chemistry." No. 36, Advances in Chemistry Series, American chemical society, Washington, D. C. 1962, pp. 143–149.

* cited by examiner

Primary Examiner—Thurman K. Page
Assistant Examiner—Blessing Fubara
(74) Attorney, Agent, or Firm—Oppenheimer Wolff & Donnelly LLP (57) ABSTRACT

Biocompatible metallic medical devices having silanized surfaces coupled to nucleophile residues that release sustained, therapeutic amounts of nitric oxide to specific sites within a mammalian body are provided. Additionally, the biocompatible metallic medical devices can also be provided with anti-thrombogenic, lubricious coatings that release sustained, therapeutic amounts of nitric oxide. Moreover, the silanized metallic devices are surprisingly durable when exposed to harsh chemical methods often needed to bind nitric oxide-releasing functional groups to nucleophile residues. Furthermore, methods are provided for producing stable, silanized, sustained nitric oxide-releasing metallic medical devices.

14 Claims, 3 Drawing Sheets figure 1 figure 2 figure 3

United States Patent
US 6,270,779 B1

NITRIC OXIDE-RELEASING METALLIC MEDICAL DEVICES

FIELD OF THE INVENTION

The present invention is directed at medical devices capable of sustained nitric oxide release. Specifically, the present invention describes implantable medical devices that release nitric oxide from their surfaces. More specifically, the present invention is directed at metallic medical devices which have NONOate groups coupled to their surfaces through siloxane intermediates.

BACKGROUND OF THE INVENTION

Nitric Oxide (NO) is a simple diatomic molecule that plays a diverse and complex role in cellular physiology. Less than 15 years ago NO was primarily considered a smog component formed during the combustion of fossil fuels mixed with air. However, as a result of the pioneering work of Ferid Murad et al. it is now known that NO is a powerful signaling compound and cytotoxic/cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOS1, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{+2}$ levels. Increased intracellular $Ca^{+2}$ concentrations result in smooth muscle relaxation which accounts for NO's vasodilating effects. Inducible NOS is responsible for the sustained release of larger amounts of NO and is activated by extracellular factors including endotoxins and cytokines. These higher NO levels are play a key role in cellular immunity.

Medical research is rapidly discovering therapeutic applications for NO including the fields of vascular surgery and intervention cardiology. Procedures used to clear blocked arteries such as percutaneous transluminal coronary angioplasty (PTCA) (also known as balloon angioplasty) and atherectomy and/or stent placement can result in vessel wall injury at the site of balloon expansion or stent deployment. In response to this injury a complex multi-factorial process known as restenosis can occur whereby the previously opened vessel lumen narrows and becomes re-occluded. Restenosis is initiated when thrombocytes (platelets) migrating to the injury site release mitogens into the injured endothelium. Thrombocytes begin to aggregate and adhere to the injury site initiating thrombogenesis, or clot formation. As a result, the previously opened lumen begins to narrow as thrombocytes and fibrin collect on the vessel wall. In a more frequently encountered mechanism of restenosis, the mitogens secreted by activated thrombocytes adhering to the vessel wall stimulate overproliferation of vascular smooth muscle cells during the healing process, restricting or occluding of the injured vessel lumen. The resulting neointimal hyperplasia is the major cause of a stent restenosis.

Recently, NO has been shown to significantly reduce thrombocyte aggregation and adhesion; this combined with NO's directly cytotoxic/cytostatic properties may significantly reduce vascular smooth muscle cell proliferation and help prevent restenosis. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylacticly. This can be accomplished by stimulating endogenous NO production or using exogenous NO sources. Methods to regulate endogenous NO release have primarily focused on activation of synthetic pathways using excess amounts of NO precursors like L-arginine, or increasing expression of Nitric oxide synthase (NOS) using gene therapy. United States patents numbers (USPN) U.S. Pat. Nos. 5,945,452, 5,891,459 and 5,428,070 describe sustained NO elevation using orally administrated L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. As previously discussed, to be effective at preventing restenosis an inhibitory therapeutic such as NO must be administered for a sustained period at therapeutic levels. Consequently, any NO-releasing medical device used to treat restenosis must be suitable for long term or permanent implantation. An ideal candidate device is the arterial stent. Therefore, a stent that safely provides therapeutically effective amounts of NO to a precise location would represent a significant advance in restenosis prevention.

Nitric oxide-releasing compounds suitable for in vivo applications have been developed by a number of investigators. As early as 1960 it was demonstrated that nitric oxide gas could be reacted with amines to form NO-releasing anions having the following general formula (1):

R—R'N—N(O)NO⁻                           (1)

wherein R and R' are ethyl. Salts of these compounds could spontaneously decompose and release NO in solution. (R. S. Drago et al *J. Am. Chem. Soc.* 1960, 82, 96–98.)

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 and in J. A. Hrabie et al, *J. Org. Chem.* 1993, 58, 1472–1476, all of which are herein incorporated by reference. Briefly, Hrabie et al. describes NO-releasing intramolecular salts (zwitterions) having the general formula (2):

RN[N(O)NO]⁻(CH₂)ₓNH₂⁺R'                      (2)

The [N(O)NO]⁻ (abbreviated herein after at NONO) containing compounds thus described release NO via a first order reaction that is predictable, easily quantified and controllable. This is in sharp contrast to other known NO-releasing compounds such as the S-nitrosothiol series as described in U.S. Pat. Nos. 5,380,758, 5,574,068 and 5,583,101.

Stable NO-releasing compounds of formula 2 have been coupled to amine containing polymers. U.S. Pat. No. 5,405,919 ("the '919 patent") describes biologically acceptable polymers that may be coupled to NO-releasing groups including polyolefins, such as polystyrene, polypropylene, polyethylene, polyterafluoroethylene and polyvinylidene, and polyethylenimine, polyesters, polyethers, polyurethanes and the like. Medical devices, such as arterial stents, composed of these polymers represent a potential means for the site-specific delivery of NO. However, polymeric stents and other medical devices are not necessarily appropriate for all in situ applications where concentrated, localized NO delivery is desired. Many applications require rigid and semi-flexible metallic devices for optimum, long-term performance.

Expandable metal stents have proven to provide better support for arteries than their polymeric counterparts. However, unlike the polymers described above, biocompatible metals such as nickel, titanium, stainless steel and mixtures thereof, do not possess reactive surface amines. Therefore, attempts have been made to provide metallic medical devices with polymeric surfaces by coating them with amine containing polymers. However, many of these methods can be expensive and may diminish the safety and effectiveness of the medical devices, especially expandable stents. Stents coated with polymers such as those described in the '919 patent can be successfully treated to provide a sustained release of NO. However, there remains a risk that the polymer covering may fracture during stent expansion and deployment. Such fractures may result in fragments being released downstream, potentially blocking narrower arteriolae. Moreover, polymer coated metallic stents are more prone to thrombogenesis development than uncoated metallic stents. Consequently, polymer coated metallic medical devices that release NO have not been widely used.

Therefore, there is a need for NO-releasing metallic medical devices that do not rely on polymeric coatings. Consequently, it is an object of the present invention to provide metallic medical devices that deliver NO to specific anatomical sites within the mammalian body.

It is another object of the present invention to provide metallic medical devices capable of sustained NO release from their surfaces without the use of polymeric coatings.

It is yet another object of the present invention to provide metallic stents capable of the sustained release of NO from their surfaces in amounts sufficient to prevent restenosis.

It is yet another object of the present invention to provide methods for preventing occlusions in arteries, thus preventing restenosis.

It is another object of the present invention to provide methods for treating ischemic heart disease and simultaneously preventing restenosis by deploying an uncoated metal stent with a NO-releasing surface.

SUMMARY OF THE INVENTION

The present invention accomplishes the above described and other objects by providing medical devices, and methods for preparing medical devices, that have silanized metallic surfaces that can be coupled to nitric oxide (NO) releasing compounds. The present invention also provides medical devices useful in the localized delivery of NO to tissues in need thereof. The medical devices of the present invention are capable of localized, sustained NO release in amounts effective to promote wound healing, treat local infections and cancer, stimulate localized vasodilation and angiogenesis, reduce inflammation and prevent proliferative diseases including restenosis.

The metallic medical devices of the present invention include, but are not limited to, arterial stents, guide wires, catheters, trocar needles, bone anchors, bone screws, protective platings, hip and joint implants, electrical leads, biosensors and probes. Suitable metallic surfaces include, but are not limited to, stainless steel, nickel, titanium, aluminum, copper, gold, silver, platinum and combinations thereof Generally, the present invention includes methods for providing the metallic medical devices with diazeniumdiolate functional groups (NONOates). In one embodiment of the present invention the metallic devices are silanized with compounds having integral nucleophile residues, such as amine-functionalized silanes, that are provided with NONOates by exposing the nucleophile bearing metallic surfaces to NO gas under pressure in an anaerobic environment (a process referred to hereinafter as diazeniumdiolation).

In another embodiment of the present invention the metallic medical devices are provided with additional nucleophile residues by first coupling reactive silanes, such as isocyanatosilanes, to the metallic surface. The medical device is then reacted with multi-functional molecules, either monomers or polymers, having nucleophile resides such as, but not limited to, and polyethylenimine. These multi-functional molecules bind to the reactive silane coated medical device. At this point the metallic medical device can be diazeniumdiolated, or alternatively, the surface can be further enriched to contain additional nucleophile residues using alternating cycles of cross-linking agents and multi-functional molecules followed by diazeniumdiolation.

In yet another embodiment of the present invention the metallic medical devices are provided with a biocompatible, antithrombogenic, lubricious, drug accommodating coating that contains nucleophile residues suitable for diazeniumdiolation. In still another embodiment of the present invention NO-releasing NONOates are trapped within polymer matrices of the present invention.

In other embodiments of the present invention, methods for preparing metallic medical devices having silanized metallic surfaces with reactive amine groups are provided. Moreover, methods for preparing metallic medical devices having biocompatible, antithrombogenic, lubricious, drug accommodating coatings containing nucleophile residues suitable for diazeniumdiolation are provided. In still another embodiment of the present invention methods for preparing metallic medical devices having polymer matrices entrapping NO-releasing NONOates therein are also provided.

Other objects, features and advantages of the present invention will be apparent to those skilled in the art from a consideration of the following detailed description of preferred exemplary embodiments thereof taken in conjunction with the Figures which will first be described briefly.

DETAILED DESCRIPTION OF THE INVENTION

Approximately thirty to forty percent of all patients undergoing percutaneous transluminal coronary angioplasty (PTCA) to recanalize occluded coronary arteries will develop secondary blockages (restenosis) at the site of repair within three to six months post PTCA. When restenosis occurs, secondary procedures such as coronary artery bypass graft surgery (CABG) may be needed to permanently correct the problem. Moreover, many patients receiving primary therapy for ischemic heart disease (reduced blood flow to the heart muscle) elect CABG due to the high rate of restenosis associated with PTCA. Generally, CABG procedures increase patient suffering, risk of mortality and associated heath care costs as compared to patients undergoing PTCA. Consequently, technologies that can reduce PTCA associated restenosis will decrease the number of primary and secondary CABG procedures and increase the potential for PTCA to offer ischemic heart disease patients improved long term prognoses. It is understood that coronary artery disease, and associated corrective vascular surgical procedures, are used as exemplary embodiments of the present invention and not intended as limitations. Furthermore the devices and methods of the present invention can be used to treat occluded arteries at any anatomical site caused by any vascular disease or traumatic event.

The localized sustained release of nitric oxide (NO) under physiological conditions can provide in situ cytostatic, antithrombogenic, vasodilatory, antiproliferative and other pharmacological effects. Localized NO delivery has become increasingly attractive as a potential anti-restenotic agent in the field of reconstructive vascular surgery including interventional cardiology. However, in order for NO to effectively reduce restenosis, it must be administered to the injured vessel wall as soon as possible after the initial insult and must be maintained for sustained periods. Consequently, the arterial stent is an ideal medical device for the sustained, localized delivery of NO and will be used as a non-limiting exemplary embodiment of the present invention.

Arterial stents have been fabricated from a variety of compounds including surgical grade metals, metallic alloys and biocompatible synthetic polymers such as polypropylene, polyethylene, polyesters, polyethers, polyurethanes and polylactides. Moreover, metallic stents having drug releasing polymeric coatings have also been proposed by the present inventors and others. However, polymeric stents present unsolved challenges in deploying at tortuous lesions, generally do not maintain vessel patency as well as metallic stents and polymeric coatings used on metallic stents may fracture during placement and deployment, potentially releasing thrombogenic nuclei and fragments into the circulatory system. Therefore, the present inventors have developed metallic medical devices and methods for making same that have NO-releasing functional groups coupled directly to the device's surface through silane intermediates.

In a broad aspect of the present invention, NO-releasing groups that are stable under physiological conditions are bound to nucleophile residues present in the backbone, or present as pendent groups attached to molecules and/or polymers covalently linked to a metal surface. The molecules and polymers having the nucleophile residues may be coupled to the metal surface covalently or non-covalently.

In one embodiment of the present invention the NO-releasing functional groups are 1-substituted diazen-1-ium-1, 2-diolates (diazeniumdiolates) referred to hereinafter as NONOates having the general formula (1):

$$RN[N(O)NO]^-(CH_2)_xNH_2^+R' \qquad (1)$$

These compounds are disclosed and described in United States Patent Serial Numbers (USPSN) U.S. Pat. Nos. 4,954,526, 5,039,705, 5,155,137, 5,212,204, 5,250,550, 5,366,997, 5,405,919, 5,525,357 and 5,650,447 issued to Keefer et al. and in J. A. Hrabie et al, *J. Org. Chem.* 1993, 58, 1472–1476, all of which have been incorporated herein by reference.

Generally, the NONOates of the present invention can be easily formed according to formula 2:

$$X^-+2NO \rightarrow X-[N(O)N(O)]^- \qquad (2)$$

where X is a nucleophile such as, but not limited to, secondary or primary amines. Suitable nucleophile containing compounds such as, but not limited to, polyethylenimine (PEI) are dissolved in non-aqueous solvents and degassed using alternative cycles of inert gas pressurization followed by depressurization under vacuum. Once the solution has been degassed, the nucleophile is exposed to nitric oxide gas under pressure. The solution's pH is maintained as required to assure the resulting diazeniumdiolate salt's stability. NONOates may be formed on solid substrates, or in solution and precipitated therefrom using an appropriate filter matrix.

In the present invention, the NONOates are formed directly on the surface of a metallic medical device to which reactive nucleophiles have been bonded. For the purposes of the present invention, bonded or coupled refers to any means of stably attaching a nucleophile containing compound to a metallic surface including, but not limited to, ionic bonds, covalent bonds, hydrogen bonds, van der Waals' forces, and other intermolecular forces. Moreover, nucleophile-containing compounds physically entrapped within matrices such as interpenetrating polymer networks and polymeric complexes are considered to be within the scope of the present invention.

The present invention teaches methods for bonding multifunctional molecules including nucleophile containing compounds to metallic surface using amine-functionalized silanes, silane intermediates bonded to nucleophiles and nucleophile containing compounds entrapped within matrices formed using silane intermediates. Without being bound to any particular theory, and not intended as a limitation, the present inventors propose that silicon atoms form covalent bonds with oxygen atoms or other sites present on the surface of the metallic medical devices. The bonds formed between the metallic surfaces and the silanizing compounds of the present invention were surprisingly found to be sufficiently stable to withstand reaction conditions necessary for the formation of NONOates. This unexpected result permits metallic medical devices, such as but not limited to, vascular stents to be provided with sustained NO-releasing groups in accordance with the teachings of the present invention.

In one embodiment of the present invention metal medical devices are provided with nucleophile functional groups directly using aminofunctional silanes, such as but not limited to, 4,7,10-triazadecyl-trimethoxysilane, trimethoxysilyl-propyldiethylene-triamine, 3-aminopropyltriethoxysilane, 3-aminopropyltrimethoxysilane, 3-aminopropyldiisopropylethoxysilane, and 3-aminopropyhnethyldiethoxysilane, available from United Chemical Technologies, Inc., Bristol, Pa. Generally, the aminofunctional silanes are dissolved in non-aqueous solvents such as but not limited to tetrahydrofuran (THF), acetonitrile or combinations therefore. The aminofunctional silane solutions are then applied to the surface of the medical devices using methods known to those skilled in the art including, but not limited to, dipping, spraying, brushing, imbibing and rolling. After the aminofunctional silane solution is applied, the metal device is dried. Drying can by conducted at room temperature, at elevated temperatures, under normal atmosphere, under a reduced atmosphere, or any combination thereof.

In another embodiment of the present invention nucleophile containing compounds are coupled to reactive isocyanatosilanes on the surface of metallic medical devices. Exemplary isocyanatosilanes included, but were not limited to, 3-isocyanatopropyltriethoxysilane and others having at least one isocyanate functional group and at least one hydrolyzable alkoxy bonded to silicon. Generally, the nucleophile is an amine donor including, but not limited to, $C_1$–$C_{10}$ cycloalkyl, alkyl and alkenyl monoamines such as methylamine, ethylamine, diethylamine, ethylmethylamine, triethylamine, n-propylamine, allylamine, isopropylamine, n-butylamine, n-butylmethylamnine, n-amylamine, n-hexylamine, 2-ethylhexylamine, cyclohexylamine, ethylenediamine, polyethylenamine, 1,4-butanediamine, 1,6-hexanediamine, n-methylcyclohexylamine, and alkenamines including ethylenimine and polyethylenimine. The amine donors of the present invention are dissolved and thoroughly mixed in suitable non-aqueous solvents such as THF, acetonitrile and combinations thereof. Next, an appropriate amount of an isocyanatosilane is added to the dissolved amine donor and the combination of solvent, amine donor and isocyanatosilane is mixed. The resulting solution is then applied to the surface of the medical device using methods known to those skilled in the art including, but not limited to, dipping, spraying, brushing, imbibing and rolling. The coated medical device is then dried at room temperature, at elevated temperatures, under normal atmosphere, under a reduced atmosphere, or any combinations thereof.

In yet another embodiment of the present invention the surfaces of the metallic medical devices of the present invention are first silanized using vinylsilane derivatives such as, but not limited to, trichlorovinylsilane dissolved in an organic solvent. The resulting silanized surface is then co-polymerized, or grafted, with (to) suitable acrylic acid derivatives forming a cross-linked hydrogel. Next a nucleophile-containing polymer and the hydrogel are co-polymerized under conditions known to those skilled in the art as appropriate for the nucleophile/hydrogel combination. The resulting surface has a multiple pendent group matrix extending in three dimensions away from the metallic surface providing numerous sites for diazeniumdiolation. The number of diazeniumdiolation sites (reactive nucleophile residues) can be further increased and the three dimensional matrix extended by treating the surface with aldehydes, such as but not limited to, glutaraldehyde or crotonaldehyde, followed by additional nucleophile containing polymer. This step can be repeated multiple times to generate a complex, three-dimensional surface having various layers of reactive nucleophiles needed for generating NO-releasing metallic medical devices having a wide range of NO-releasing capacities and longevity.

Briefly, the diazeniumdiolates (NONOates) of the present invention are formed by reacting the previously processed metallic medical devices (devices provided with nucleophile residues in accordance with the teachings of the present invention) with NO gas under pressure in an anaerobic environment.

It is also possible to entrap NO-releasing compounds within polymer matrices formed on the surface of the metallic medical devices using the teachings of the present invention. For example all acetonitrile/THF soluble diazeniumdiolates or other NO-releasing compounds known to those of ordinary skill in the art can be entrapped within polyurethane, polyurea and/or other polymeric matrices on the surface of the metallic medical devices of the present invention. For example, and not intended as a limitation, a polyisocyanate, specifically an aromatic polyisocyanate based on toluene diisocyanate dissolved in a polymer/solvent solution, is added to a mixture containing a saturated polyester resin (polyol), at least one non-aqueous solvent, a NO-releasing compound and a suitable isocyanatosilane. The solution is mixed and the metallic medical device is coated with the solution and then dried. Suitable polyisocyanates include, but are not limited to, m-xylylene diisocyanate, m-tetramethylxylxylene diisocyanate (meta-TMXDI available from Cytec Industries, Inc., Stamford, Conn.) and Desmodur® CB 60N (available from Baeyer Pittsburgh, Pa.). Polyols useful in this invention include, but are not limited to, polyester polyols, polyether polyols, modified polyether polyols, polyester ether polyols, caster oil polyols, and polyacrylate polyols, including Desmophen® 1800, A450, A365 and A160 (available from Baeyer Pittsburgh, Pa.).

In one embodiment of the present invention, the lubricious, drug-accommodating coating disclosed and described above and in U.S. patent application Ser. No. 09/405024, filed Sep. 27, 1999, the entire contents of which are hereby incorporated by reference, can be used to bind the diazeniumdiolate MOM-PIPERAZI/NO (see J. E. Saaverdra, et al. 2000. *Conversion of a Polysaccharide to Nitric Oxide-Releasing Form. Dual Mechanism Anticoagulant Activity of Diazeniumdiolated Heparin. Bioorganic & Medicinal Chemistry Letters* 10:1–3, the entire contents of which are herein incorporated by reference). The resulting medical device will provide sustained NO release when exposed to physiological conditions without requiring further processing.

The resulting diazeniumdiolated metallic medical devices made in accordance with the teaching of the present invention are then tested to determine the concentration and duration of NO release upon exposure to physiological conditions (immersion in phosphate buffered saline, pH 7.4 at 37° C.). Nitric oxide gas is detected and quantified using the chemiluminescence methods described in Keefer, L. K., Nims, R. W., Davies, K. M. and D. A. Wink. 1996. *NONOates*(1-*Substituted Diazen*-1-*ium*-1, 2 *diolates*) *as Nitric Oxide Donors: Convenient Nitric Oxide Dosage Forms.* Methods in Enzymology. Vol 28:281–293, the entire contents of which are incorporated herein by reference.

The following non-limiting examples are provided to more precisely define the methods and devices of the present invention. Detailed procedures are provided for the different silanization and diazeniumdiolation methods provided above. It is understood that there may be other methods and devices for practicing the present invention that are not included in the following detailed examples. These methods and devices, as well as others, are considered to be within the scope of the present invention. Moreover, the reagent concentrations and reaction conditions including times, temperatures and atmospheres are not intended as limitations, but merely as exemplary embodiments. Many different reactants, reagent concentrations and reaction conditions may be employed without departing from the spirit of the present invention.

EXAMPLES

Example 1

Preparation of the Metallic Surfaces Prior to Silanization

Metal stents to be silanized in accordance with the teachings of the present invention are cleaned as followed. Stents are completely immersed in hexane (available from Sigma Chemical, St. Louis, Mo.) and sonicated for 15 minutes in an ultrasonic bath. Next, the stent is removed from the hexane and immersed in 2-propanol (available from Sigma Chemical, St. Louis, Mo.) and sonicated as before. The stent is then thoroughly rinsed in distilled water prior to being immersed in 1 N sodium hydroxide (available from Sigma Chemical, St. Louis, Mo.) and sonicated for an additional 15 minutes in an ultrasonic bath. The stent is again thoroughly washed in distilled water and then dried overnight at 40° C. under vacuum.

Example 2

Method for Providing Metallic Medical Devices with an Amino-functional Silane Coating Into a small clean non-reactive vial, add 5 g trimethoxysilyl-propyldiethylene-triamine (available from United Chemical Technologies, Inc., Bristol, Pa. catalogue number T-2910), 7 g acetonitrile and 3 g THF (both available from Sigma Chemicals, St. Louis, Mo.), mix thoroughly for 15 minutes or until all of the trimethoxysilyl-propyldiethylene-triamine is in solution. Dip a previously cleaned stent into the saline solution for 10 seconds. Remove the stent from the silane solution, drain, and allow to dry for 30 minutes in a well ventilated area. Next the stent is dried over night at 40° C. under vacuum.

Example 3

Providing a Metallic Medical Device with a Polyethylenimine (PEI) Direct Coating Into a small clean non-reactive vial, add a predetermined amount of PEI (available from Aldrich Chemicals, St. Louis, Mo. catalogue number 46853-3), 7 g acetonitrile and 3 g THF. Mix thoroughly for 15 minutes or until all of the PEI is in solution. Next, add 0.2 g of 3-isocyanatopropyltriethoxysilane (available from United Chemical Technologies, Inc., Bristol, Pa. catalogue number I-7840) to the PEI/solvent solution. Mix for an additional three minutes using a roller mixer. Dip a previously cleaned stent into the silane solution for 10 seconds. Remove the stent from the silane solution, drain, and allow to dry for 30 minutes in a well ventilated area. Next the stent is dried over night at 40° C. under vacuum.

Example 4

Providing a Metallic Medical Device with PEI Grafted to a Hydrogel Coating a) Silanization: Metallic stents are cleaned as in Example 1, followed by immersing the cleaned stent in a solution containing 3 g of trichlorovinylsilane (available from United Chemical Technologies, Inc., Bristol, Pa. catalogue number V-4900) dissolved in 100 g xylenes (available from Sigma Chemical, St. Louis, Mo.).

b) Forming the Hydrogel Coating: A hydrogel coating is formed by immersing the silanized stent in a solution containing 35 g of acrylic acid (available from Aldrich Chemicals, St. Louis, Mo. catalogue number 14723-0), 5 g of acrylamide, (available from Aldrich Chemicals, St. Louis, Mo. catalogue number 14857-1) and 3.1 g 0.1M ceric ammonium nitrate (available from Aldrich Chemicals, St. Louis, Mo. catalogue number 22954-7) in 65 mL of distilled water.

c) Grafting PEI to the Hydrogel Coated Stent: The stents are then treated with a 2.5% PEI solution containing 0.1M 1,[-3-(Dimethylamino)propyl-]3-ethylcarbodiimide hydrochloride (available from Aldrich Chemicals, St. Louis, Mo. catalogue number 16146-2) in sodium tetraborate (available from Aldrich Chemicals, St. Louis, Mo. catalogue number 22133-3) (pH 9.2) for 0.5 hours. Stents prepared in this fashion are suitable for cross-linking to more fully develop the resulting three dimensional surface. The stents are prevented from dehydration and stored wet until processed further.

d) Cross-linking PEI with Aldehydes: The wet stents are immersed in 5% w/w glutaraldehyde (available from Aldrich Chemicals, St. Louis, Mo. catalogue number 34085-5) in 0.1M sodium borate in distilled water (pH 9.2) and held at room temperature for one hour.

e) Providing Cross-linked Three Dimensional Matrix with Nucleophile Residues:

The wet, cross-linked stents are thoroughly rinsed in distilled water and treated with a 2.5% w/w PEI solution containing 0.5% NaBH$_3$CN (available from Aldrich Chemicals, St. Louis, Mo. catalogue number 15615-9) in 0.2M hemisodium HEPES (available from Aldrich Chemicals, St. Louis, Mo. catalogue number 23388-9) in distilled water (pH 7.4). The reaction is allowed to proceed over night at room temperature. Finally, the stents are thoroughly rinsed in distilled water and dried at 50° C. over night

Example 5

Providing Metallic Stents with Anti-thrombogenic, Lubricious Coatings Having Nucleophile Residues a) Silanization: Metallic stents are cleaned as in Example 1, followed by immersing the cleaned stents in a solution containing 3 g of trichlorovinylsilane dissolved in 100 g xylenes.

b) Forming the Hydrogel Coating: A hydrogel coating is formed by immersing the silanized stents in a solution containing 35 g of acrylic acid, 5 g of acrylamide, and 3.1 g 0.1M ceric ammonium nitrate in 65 mL of distilled water.

c) Grafting PEI to the Hydrogel Coated Stent: The stents are then treated with a 2.5% PEI solution containing 0.1M sodium borate (pH 9.2) for 0.5 hours. Stents prepared in this fashion are suitable for cross-linking to more fully develop the resulting thee dimensional surface. The stents are prevented from dehydration and stored wet until processed further.

d) Applying the Anti-thrombogenic Coating: A solution containing 1.5 g sodium heparin (available from Sigma Chemicals, St. Louis, Mo. catalogue number H-3393) and 49.5 mg of sodium periodate (available from Aldrich Chemical Company, Milwaukee, Wis.) in 300 mL of 0.05 M phosphate buffer (pH 6.88; 0.25 M $Na_2HPO_4$ and 0.25 M $KH_2PO_4$, both available from Sigma Chemicals, St. Louis, Mo.) is mixed thoroughly until all reagents are dissolved. The solution is gently preheated to a temperature of 50° C. Previously cleaned stents are immersed in the preheated heparin solution and held at 50° C. for approximately 10 minutes. Next, 0.1 mg/mL of $NaBH_3CN$ is added to the heparin solution containing the stents and the coupling reaction is allowed to proceed for approximately two hours at 50° C. The stents are then thoroughly rinsed in distilled water and dried overnight at room temperature.

Example 6

One Step Polyurethane Coating Containing MOM-PIPERAZI/NO

A coating solution containing 1.10 g of Desmodur® CB 60N (available from Baeyer Pittsburgh, Pa. catalogue number D-051), 2.86 g Desmophen® 1800 (available from Baeyer Pittsburgh, Pa. catalogue number D-018) and 0.10 g MOM-PIPERAZI/NO (NIH/NCI, Frederick, Md.) is prepared in 7.76 g acetonitrile and 2.64 g THF and mixed for fifteen minutes, or until all reagents are dissolved. Next 0.204 g of 3-isocyanatopropyltriethoxysilane (available from United Chemical Technologies, Inc., Bristol, Pa.) is added to the coating solution and the solution is mixed for an additional three minutes, or until all of the reagents are in solution.

Previously cleaned metallic stents are immersed in the coating solution for approximately 10 seconds and then dried for 30 minutes at room temperature in a well ventilated area. The coated stents are then dried overnight at 40° C. under vacuum.

Example 7

Diazeniumdiolation of Metallic Medical Devices Previously Provided with Nucleophile Residues Substituted Ammonium Diazeniumdiolated PEI (MW 600,000 to 1,000,000)-coated Stainless Steel Medical Coupon A 10 mm×30 mm PEI (MW 600,000 to 1,000,000)-coated stainless steel coupon from Example 4 is placed in a 13 mm×100 mm glass test tube. Ten ml of acetonitrile is added to the test tube, which was then placed in a 250 ml Parr® hydrogenation vessel and transferred to a NO apparatus. The vessel is degassed by repeated cycles (×10) of pressurization with nitrogen gas at 4 atmospheres and depressurization with 10 mm of Hg vacuum. Next, the vessel undergoes 10 cycles of pressurization with NO at 4 atmospheres and depressurization with a vacuum of 10 mm of Hg. Finally, the vessel is filled with NO at 4 atmospheres and left at room temperature for 48 hrs.

After 48 hrs, the vessel is purged of NO and pressurized/depressurized with repeated cycles (×10) of nitrogen gas at 4 atmospheres. The test tube is removed from the vessel and the acetonitrile solution decanted. The coupon is then washed with 10 ml of acetonitrile (×1) and 10 ml of diethyl ether (×3). The coupon is then removed from the test tube and dried under a stream of nitrogen gas. This procedure results in a substituted ammonium form of diazeniumdiolated PEI (MW range 600,000 to 1,000,000)-coated stainless steel coupon.

Figure 1:
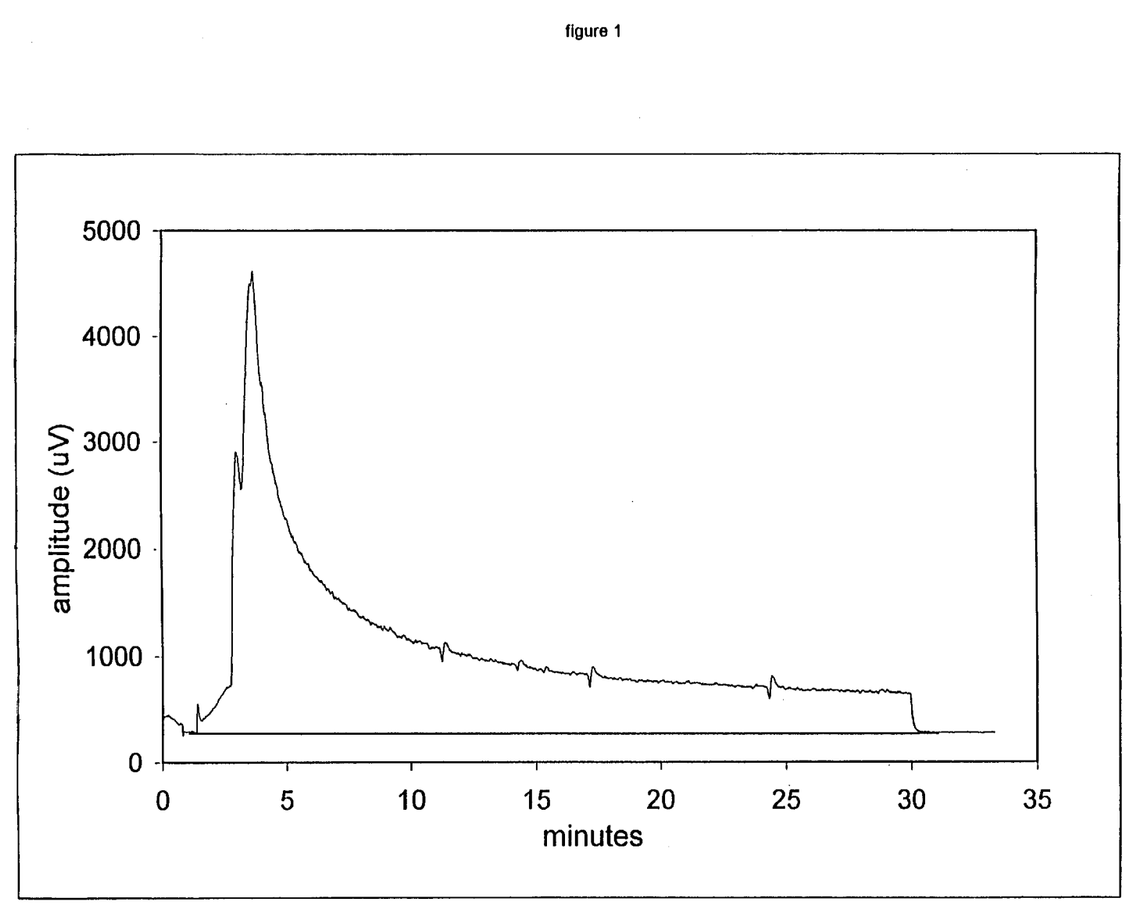
FIG. 1 graphically depicts the chemiluminescence detector response to nitric oxide generated from the nucleophile residue-bound nitric oxide-releasing $N_2O_2^-$ functional group containing the metallic coupon of Example 7.

The diazeniumdiolated PEI (MW range 600,000 to 1,000,000)-coated coupon was cut into two equal pieces. One piece, weighing 75.02 mg, was immersed in phosphate buffer, pH 7.4 at 37° C., whereupon chemiluminescence-detectable NO as shown in FIG. 1 was evolved during a 370 minute period of analysis. The total NO was measured at 17.5 nmoles or 233 pmole/mg.

Example 8

Diazeniumdiolation of Metallic Medical Devices Previously Provided with Nucleophile Residues Sodium Salt of a Diazeniumdiolated PEI (MW range 600,000 to 1,0000,004)-coated Stainless Steel Coupon A 10 mm×30 mm PEI (MW 600,000 to 1,000,000)-coated stainless steel coupon from Example 4 is placed in a 13 mm×100 mm glass test tube. Ten ml of 3% sodium methylate in methanol or acetonitrile is added to the test tube, which is then placed in a 250 ml stainless steel Parr® hydrogenation vessel. The vessel is degassed by repeated cycles (×10) of pressurization/depressurization with nitrogen gas at 10 atmospheres. Next, the vessel undergoes 2 cycles of pressurization/depressurization with NO at 30 atmospheres. Finally, the vessel is filled with NO at 30 atmospheres and left at room temperature for 24 hrs.

After 24 hrs, the vessel is purged of NO and pressurized/depressurized with repeated cycles (×10) of nitrogen gas at 10 atmospheres. The test tube is removed from the vessel and the 3% sodium methylate solution is decanted. The coupon is then washed with 10 ml of methanol (×1) and 10 ml of diethyl ether (×3). The coupon is then removed from the test tube and dried under a stream of nitrogen gas. This procedure results in a sodium salt of a diazeniumdiolated PEI (MW range 600,000 to 1,000,000)-coated stainless steel coupon.

Figure 2:
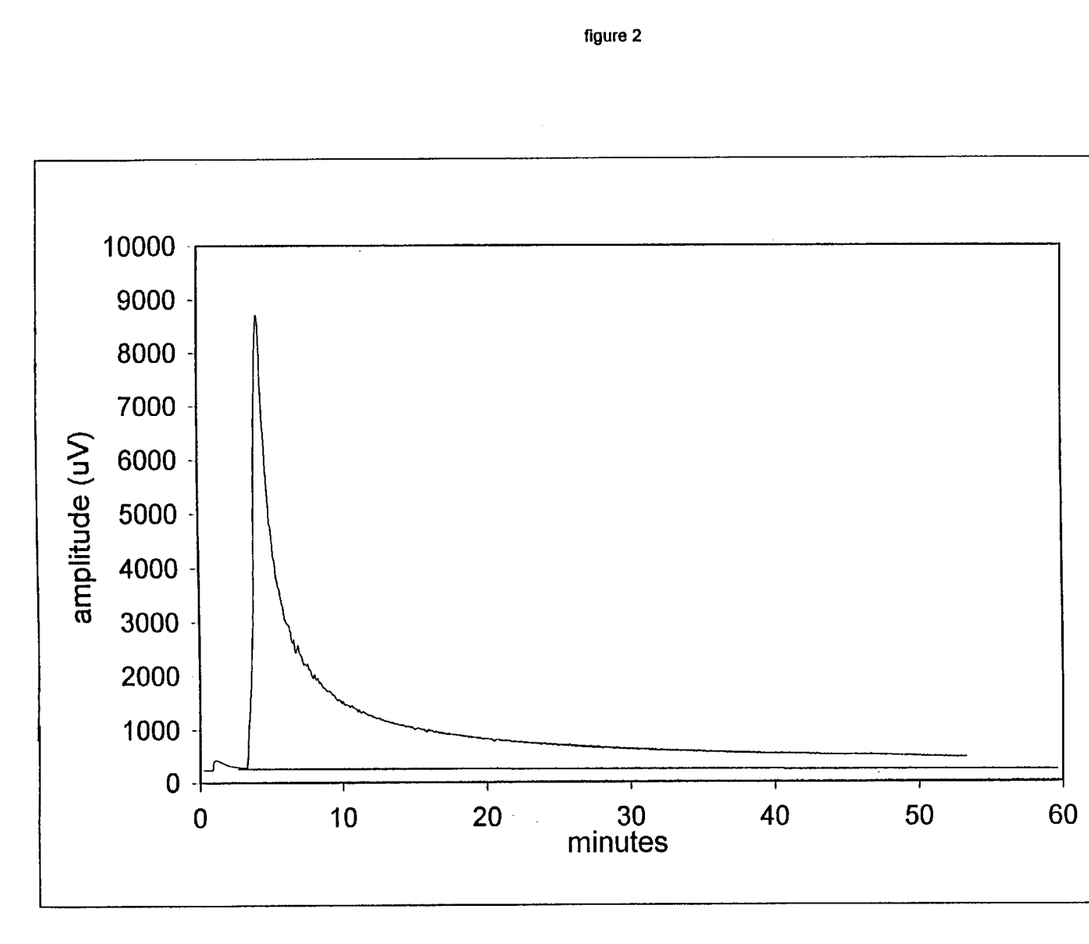
FIG. 2 graphically depicts the chemiluminescence detector response to nitric oxide generated from the nucleophile residue-bound nitric oxide-releasing $N_2O_2^-$ functional group containing the metallic coupon of Example 8.

The diazeniumdiolated PEI (MW range 6,000 to 1,000,000)-coated coupon is cut into two pieces. One piece, weighing 96.34 mg, was immersed in phosphate buffer, pH 7.4 at 37° C., whereupon chemiluminescence-detectable NO as shown in FIG. 2 was evolved during a 367 minute period of analysis. The total NO was measured at 29.1 nmoles or 302 pmole/mg.

Example 9

Diazeniumdiolation of Metallic Medical Devices Previously Provided with Nucleophile Residues Substituted Ammonium Diazeniumdiolated Siloxane of a Propyldiethylene triamine-Coated Stainless Steel Coupon A 10 mm×30 mm stainless steel coupon from Example 2 is placed in a 13 mm×100 mm glass test tube. Ten ml of tetrahydrofuran is added to the test tube, which is then placed in a 500 ml glass Parr® hydrogenation vessel and transferred to a NO apparatus. The vessel is degassed by repeated cycles (×10) of pressurization with nitrogen gas at 4 atmospheres and depressurization with 10 mm of Hg vacuum. Next, the vessel undergoes 10 cycles of pressurization with NO at 4 atmospheres and left at room temperature for 48 hrs.

After 48 hrs, the vessel is purged of NO and pressurized/depressurized with repeated cycles (×10) of nitrogen gas at 4 atmospheres. The test tube is removed from the vessel and the THF solution decanted. The coupon is then washed with 10 ml of THF (×1) and 10 ml of diethyl ether (×3). The coupon is then removed from the test tube and dried under a stream of nitrogen gas. This procedure results in a substituted ammonium form of the Diazeniumdiolated stainless steel coupon.

Figure 3:
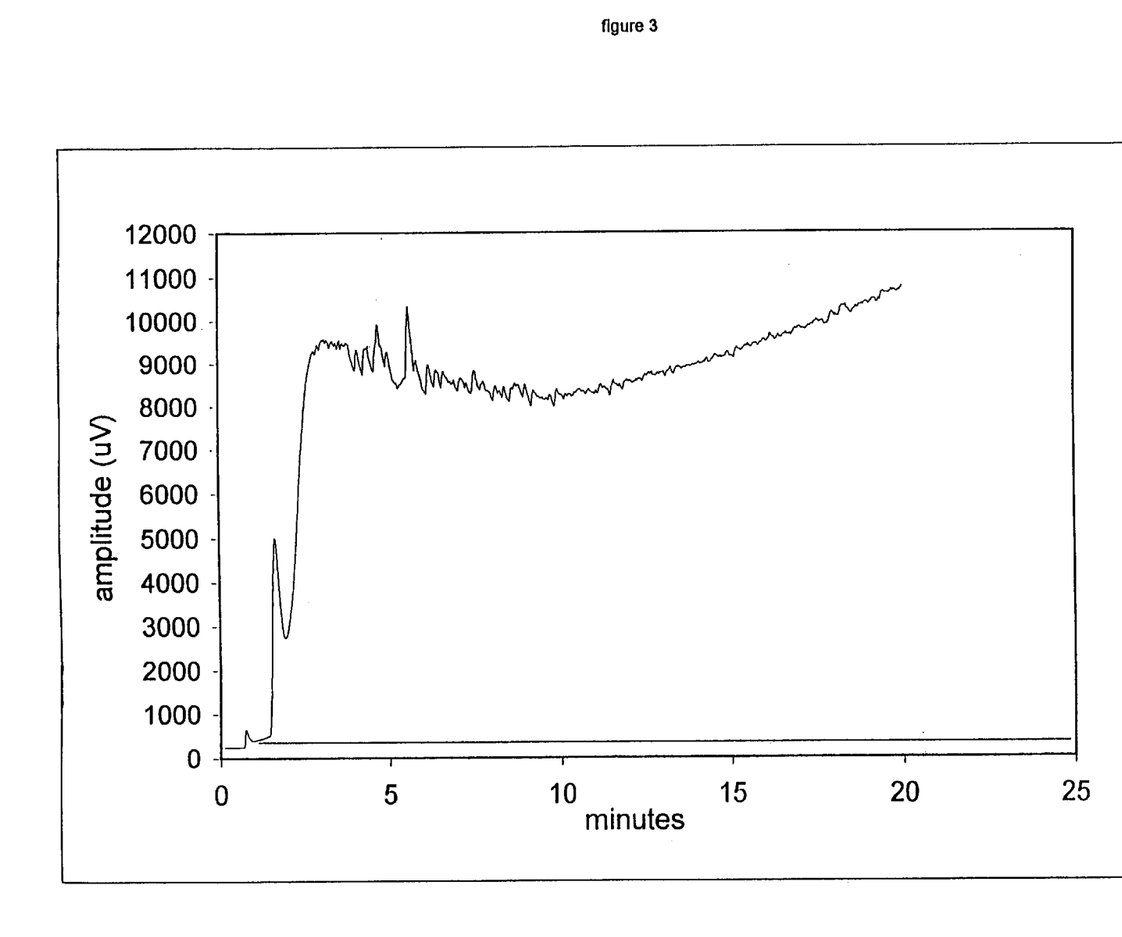
FIG. 3 graphically depicts the chemiluminescence detector response to nitric oxide generated from the nucleophile residue-bound nitric oxide-releasing $N_2O_2^-$ functional group containing the metallic coupon of Example 9.

The Diazeniumdiolated coupon is cut into two equal pieces. One piece, weighing 118.02 mg, was immersed in phosphate buffer, pH 7.4 at 37° C., whereupon chemiluminescence-detectable NO as shown in FIG. 3 was evolved during a 1.87 day period of analysis. The total NO is measured at 0.29 µmoles or 2.46 nmole/mg.

The preceding examples used silane intermediates to covalently bind functional amine groups to metallic surfaces. However, other means of providing stable, covalently bound amines on metallic surfaces are also considered within the scope of the present invention. For example, and not intended as a limitation, metal surfaces such as gold can be modified using sub-equimolar amounts of thiirane to generate a thiolated surface that can be further reacted modified with PEI. See, for example, U.S. Pat. No. 5,229,172, the entire contents of which are herein incorporated by reference. The resulting amine groups are then suitable for diazeniumdiolation in accordance with the teachings of the present invention. Moreover, plasma deposition techniques, as taught, for example, in Chandy, T. et al 2000 *Use of Plasma Glow for Surface-Engineering Biomolecules to Enhance Biocompatibility of Dacron and PTFE Vascular Prosthesis*. Biomaterials 21:699–712 (the entire contents of which are herein incorporated by reference), can also be used to create a variety of functional groups on metal surfaces that can be later modified with polyamines then diazeniumdiolated. In its broadest sense, the present invention provides metallic surfaces having NO releasing groups stably bound to thereto. The present invention can be used to provide a variety of medical devices with sustained NO-releasing surfaces suitable for therapeutic and prophylactic applications. Numerous different methods for providing NO-releasing medical devices have been described in detail. The specific method used for a given application is dictated by the composition of the surface to be coated the medical indication for the device and the pharmacology of the compounds selected. Therefore, it is apparent that while a preferred embodiment of the present invention has been shown and described, various modifications and changes may be made without departing from the true spirit and scope of the invention.

We claim:

1. A method for preparing a nitric oxide-releasing metallic surface comprising:
   a) stably binding a nucleophile residue to a metallic surface; and
   b) reacting said surface having a nucleophile residue with nitric oxide gas.

2. The method for preparing a nitric oxide-releasing metallic surface of claim 1 wherein said metallic surface is stainless steel.

3. The method for preparing a nitric oxide-releasing metallic surface of claim 1 wherein said nucleophile residue is an aminofunctional silane selected from the group consisting of 4,7,10-triazadecyl-trimethoxysilane, 3-aminopropyltriethoxysilane, 3-aminopropyltrimethoxysilane, 3-aminopropyldiisopropylethoxysilane, and 3-aminopropylmethyldiethoxysilane.

4. The method for preparing a nitric oxide-releasing metallic surface of claim 1 wherein said surface having a nucleophile residue is reacted with said nitric oxide gas under an anaerobic pressurized environment.

5. A method for preparing a nitric oxide-releasing metallic surface comprising:
   a) silanizing a metallic surface;
   b) bonding a nucleophile containing compound to said silanized metallic surface; and
   c) reacting said nucleophile containing compound bonded to said silanized metallic surface with nitric oxide gas.

6. The method for preparing a nitric oxide-releasing metallic surface of claim 5 wherein said silanizing step further comprises reacting said metallic surfaces with a silanizing compound selected from the group consisting of a vinylsilane and an isocyanatosilane.

7. The method for preparing a nitric oxide-releasing metallic surface of claim 6 wherein said vinylsilane is trichlorovinyl silane.

8. The method for preparing a nitric oxide-releasing metallic surfaces of claim 6 wherein said isocyanatosilane is 3-isocyanatopropyl-triethoxysilane.

9. The method for preparing a nitric oxide-releasing metallic surface of claim 5 wherein said nucleophile containing compound is selected from the group consisting of $C_1$–$C_{10}$ cycloalkyl, alkyl and alkenyl monoamines, methylamine, ethylamine, diethylamine, ethylmethylamine, triethylamine, n-propylamine, allylamine, isopropylamine, n-butylamine, n-butylmethylamine, n-amylamine, n-hexylamine, 2-ethylhexylamine, cyclohexylamine, ethylenediamine, polyethyleneamine, 1,4-butanediamine, 1,6-hexanediamine, n-methylcyclohexylamine, alkeneamines, ethyleneimine and polyethylenimine.

10. The method for preparing a nitric oxide-releasing metallic surface of claim 5 further comprising:
   cross-linking said nucleophile residue containing compound prior to reacting said nucleophile with said nitric oxide gas;
   reacting said cross-linked nucleophile containing compound with at least one nucleophile compound to enrich said metallic surface with additional nucleophile residues; and
   reacting said metallic surface with additional nucleophile residues with nitric oxide gas.

11. The method for preparing a nitric oxide-releasing metallic surface of claim 5 wherein said surface having a nucleophile residue containing silane is reacted with said nitric oxide gas under an anaerobic pressurized environment.

12. A method for preparing a nitric oxide-releasing metallic surface comprising:
   a) reacting a metallic surface with a mixture comprising at least one polyisocyanate, at least one polyester resin, at least one non-aqueous solvent, at least one isocyanatosilane and at least one diazeniumdiolate containing compound;

b) mixing said mixture for a time sufficient to dissolve all compounds soluble in said at least one solvent; and c) applying said mixture to said metallic surface.

13. Medical devices for delivering nitric oxide in therapeutic concentrations for sustained periods of time comprising: metallic surfaces having nitric oxide releasably bound thereto through diazeniumdiolated nucleophiles coupled to silane intermediates, said silane intermediates being bound to said metallic surface.

14. The medical devices for delivering nitric oxide in therapeutic concentrations for sustained periods of time of claim 13 wherein said medical device is selected from the group consisting of arterial stents, guide wires, catheters, trocar needles, bone anchors, bone screws, protective platings, hip and joint implants, electrical leads, biosensors and probes.

* * * * *